United States Patent [19]

Lange

[11] Patent Number: 5,326,899
[45] Date of Patent: Jul. 5, 1994

[54] PROCESS FOR PREPARATION OF IODOPROPARGYL CARBAMATES

[75] Inventor: Barry C. Lange, Lansdale, Pa.

[73] Assignee: Rohm and Haas Company, Philadelphia, Pa.

[21] Appl. No.: 76,561

[22] Filed: Jun. 14, 1993

[51] Int. Cl.$^5$ ............................................. C07C 261/00
[52] U.S. Cl. ...................................... 560/167; 558/417
[58] Field of Search ...................... 560/167, 22, 29, 30, 560/33; 558/417, 416; 564/217

[56] References Cited

U.S. PATENT DOCUMENTS

| 3,923,870 | 12/1975 | Singer | 260/482 |
| 4,661,632 | 4/1987 | Oeckl et al. | 564/217 |
| 4,841,088 | 6/1989 | Kusaba et al. | 558/417 |

FOREIGN PATENT DOCUMENTS

| 14032 | 1/1979 | European Pat. Off. |
| 539092 | 4/1993 | European Pat. Off. |
| 2220000 | 8/1989 | United Kingdom |

Primary Examiner—Arthur C. Prescott
Attorney, Agent, or Firm—Michael B. Fein

[57] ABSTRACT

A Process for producing N-alkyl iodopropargyl carbamate comprising:
A. reacting a dialkyl($C_1$–$C_3$) carbonate with propargyl alcohol in the presence of a first catalyst under conditions to produce dipropargyl carbonate;
B. reacting said dipropargyl carbonate with an alkyl($C_1$–$C_6$)amine, optionally in the presence of a second catalyst, to produce N-alkyl($C_1$–$C_6$) propargyl carbamate;
C. reacting said N-alkyl($C_1$–$C_6$) propargyl carbamate with an iodinating agent to produce N-alkyl($C_1$–$C_6$) iodopropargyl carbamate is disclosed.

10 Claims, No Drawings

PROCESS FOR PREPARATION OF IODOPROPARGYL CARBAMATES

BACKGROUND OF THE INVENTION

A. Field of the Invention

This invention is in the field of chemical processes for preparation of iodopropargyl carbamates.

B. Description of the Prior Art

Polyphase® fungicide is one of the leading paint mildewcides in the market place currently. The active ingredient is N-butyl iodopropargyl carbamate.

Troy Chemical Corporation U.S. Pat. No. 3,923,870 discloses what is presumed to be the commercial process for preparing N-butyl iodopropargyl carbamate. ICI European Pat. Appl. 0014032 published Jun. 6, 1990 discloses reacting an alkynol with an isocyanate and followed by iodination. The Troy and ICI disclosed processes use butyl isocyanate which is presumably produced from the reaction of butyl amine with phosgene. Isocyanates are generally toxic and are hazardous materials to handle. Troy's more recent process patent, GB 222 0000 published Jun. 23, 1989, discloses a method which uses as a starting material alkynyl chloroformate which is presumably produced from the reaction from propargyl alcohol and phosgene. Alkynyl chloroformate is also toxic, unstable, and hazardous. Although phosgene is a cheap raw material, it is also a very hazardous material. Presumably the cost of production of N-butyl iodopropargyl carbamate is greatly influenced by the procedures necessary for the safe handling of phosgene.

EP patent publication 0539092 A (U.S. Ser. No. 07/782,039) assigned to Rohm and Haas, the same assignee as the present invention, also discloses a process for the preparation of N-butyl iodopropargyl carbamate that avoids the use of phosgene and isocyanates.

II. SUMMARY OF THE INVENTION

It is an object of the present invention to provide an improved process for preparation of iodopropargyl carbamates. A further object is to provide such a process wherein phosgene or butyl isocyanate need not be handled. Production of N-butyl iodopropargyl carbamate is also an object of a preferred embodiment of the invention. A still further object is to provide a process which does not require the hazardous raw materials used in prior art processes. A still further object is to provide a process which does not require the use of an additional solvent and allows for the recycling of propargyl alcohol.

These objects and others which will become apparent from the following disclosure are achieved by the present invention which comprises in one aspect a process for preparing N-alkyl iodopropargyl carbamate compounds comprising:

A. reacting a dialkyl($C_1$–$C_3$) carbonate with propargyl alcohol in the presence of a first catalyst under conditions to produce dipropargyl carbonate;

B. reacting said dipropargyl carbonate with an alkyl($C_1$–$C_6$)amine, optionally in the presence of a second catalyst, to produce N-alkyl($C_1$–$C_6$)propargyl carbamate;

C. reacting said N-alkyl($C_1$–$C_6$) propargyl carbamate with an iodinating agent to produce N-alkyl($C_1$–$C_6$) iodopropargyl carbamate.

III. DETAILED DESCRIPTION OF THE INVENTION AND THE PREFERRED EMBODIMENTS

While process can be used to produce N-alkyl iodopropargyl carbamates, the preferred product is N-butyl iodopropargyl carbamate.

The process of the invention is preferably run in the absence of a solvent. However, if desired, a solvent could be used. Suitable solvents are those with boiling points higher than the alcohol released during the first step of the reaction. In the case of dimethyl carbonate, methanol is released; in the case of diethyl carbonate, ethanol is released and propanol is released in the case of dipropyl carbonate. Examples of suitable solvents are propargyl alcohol, aromatic hydrocarbons, glymes, high boiling alkanes, and the like. By aromatic hydrocarbons is meant toluene, xylene, and the like. By glymes is meant diglyme, triglyme, and the like. By high boiling alkanes is meant decalin and the like. Azeotropes of suitable solvents are also contemplated, provided the boiling point is as specified for the solvents above.

The preferred carbonates are dimethyl carbonate and diethyl carbonate.

Suitable first catalysts are any which promote the desired reaction. A number of such catalysts are known in the art. Examples of suitable first catalysts are boron tribromide, trimethylsilyliodide/iodine, potassium cyanide, $Al_2O_3$, ammonia, n-butyl lithium, alkali metal alkoxide, potassium t-butoxide/molecular sieves, dimethylaminopyridine, $Ti(OCH_2CH_3)_4$, sulfuric acid, p-toluenesulfonic acid, and the like. Suitable alkali metal alkoxides are sodium or potassium methoxide, sodium or potassium ethoxide, and the like.

The preferred alkyl amine is n-butyl amine.

Suitable optional second catalysts are any which promote the desired reaction and may either be acids or bases. Preferred second catalysts are carboxylic acids with acetic acid being most preferred.

Iodination may be performed by a variety of methods and reagents known in the literature. These methods include using iodine or an iodine releaser. Suitable iodine releasers are iodine/amino compounds, such as iodine/morpholine complex, and N-iodosuccinimide. Iodine and N-iodosuccinimide are preferred reagents.

When iodine or an iodine/amino complex is used, base should also be used and solvent such as methanol, ethanol, and aqueous ethanol should be used. Suitable bases include sodium carbonate, potassium carbonate, sodium hydroxide, and potassium hydroxide. Preferred bases are sodium or potassium hydroxide. When N-iodosuccinimide is used, a catalyst, such as silver nitrate or the like, should be used in the presence of a solvent such as acetone, methyl ethyl ketone, tetrahydrofuran, and the like. The preferable method of iodination is to react iodine with N-alkyl($C_1$–$C_6$) propargyl carbamate in the presence of sodium hydroxide.

The first step in the process comprises reacting a dialkyl($C_1$–$C_3$) carbonate with propargyl alcohol and a first catalyst at reflux to yield dipropargyl carbonate. Suitable ranges of amounts of propargyl alcohol are from about 5 to about 20 molar equivalents based upon dialkylcarbonate, with 10 molar equivalents being preferred. Suitable ranges of amounts of a first catalyst are from about 0.005 to about 0.05 molar equivalents based on dialkylcarbonate. The preferred amount of first catalyst is 0.01 molar equivalents. The reaction is considered complete when the alcohol($C_1$–$C_3$) released during the reaction stops distilling off. To the reaction mixture is added from about 2 to about 10 molar equivalents of a alkyl($C_1$–$C_6$)amine, based on the carbonate produced in the first step. The preferred amount of alkyl($C_1$–$C_6$)amine is 3 molar equivalents. Optionally, a second catalyst may be added. This second step of the reaction is carried out at from 50° to about 115° C. until the reaction is complete (1–24 hrs.).

The iodination step is carried out at temperatures of about 0° to about 25° C. for about 20 minutes to about 24 hours.

The following example illustrates a few embodiments of the invention; however, the invention should not be construed as being limited to these few illustrative embodiments.

EXAMPLE

Synthesis of N-Butyl Iodopropargyl Carbamate

A. A vessel is charged with dimethyl carbonate (10 g) and 10 mole equivalents of propargyl alcohol and 0.01 mole equivalent of sodium methoxide. The reaction mixture is heated at reflux with stirring and nitrogen atmosphere until the methanol has stopped distilling. Excess propargyl alcohol is distilled off. The residue is colled to ambient temperature. To this cooled material is added n-butylamine (3 molar equivalents). The mixture is heated to 115° C. for 8 hours. The residual propargyl alcohol and excess n-butylamine are distilled off under reduced pressure for recycling. The resultant oil is taken up in ethyl acetate, washed with water, dried over $MgSO_4$, filtered, and cleaned up with column chromatography (silica gel with ethyl acetate as eluant) to yield a colorless oil.

B. Iodine (3.3 g, 0.013 mole) is added in portions to a stirred solution of the N-butyl propargyl carbamate (4.0 g, 0.026 mole), prepared as above, in ethanol (25 ml), water (10 ml) and 50% sodium hydroxide (2.1 g, 0.026 mole) at 0°–5° C. At the end of the iodine addition, the mixture is stirred at the same temperature for another 5 min. A commercial bleach (18.3 g, 5.25%, 0.013 mole) is then added dropwise to the above solution keeping the temperature at 0°–5° C. At the end of the bleach addition, the light yellow solution is stirred at the same temperature for one hour. Extraction with methylene chloride (2×70 ml) and evaporation of the solvent on a rotary evaporator gives a crystalline residue. Crystallization from hexane/toluene gives the N-butyl iodopropargyl carbamate as needles.

While the invention has been described in sufficient detail for those skilled in the art to be able to make and use it, various alternatives, modifications, and improvements should become apparent from the foregoing disclosure without departing from the spirit and scope of the invention.

I claim:

1. Process for producing N-alkyl iodopropargyl carbamate comprising:
   A. reacting a dialkyl($C_1$–$C_3$) carbonate with propargyl alcohol in the presence of a first catalyst under conditions to produce dipropargyl carbonate;
   B. reacting said dipropargyl carbonate with an alkyl($C_1$–$C_6$)amine to produce N-alkyl($C_1$–$C_6$) propargyl carbamate;
   C. reacting said N-alkyl($C_1$–$C_6$) propargyl carbamate with an iodinating agent to produce N-alkyl($C_1$–$C_6$) iodopropargyl carbamate.

2. Process according to claim 1 wherein said dialkyl carbonate is selected from the group consisting of dimethyl carbonate and diethyl carbonate.

3. Process according to claim 1 wherein said alkyl($C_1$–$C_6$)amine is butylamine.

4. Process according to claim 1 wherein said first catalyst is selected from the group consisting of boron tribomide, trimethylsilyliodide/iodine, potassium cyanide, $Al_2O_3$, ammonia, n-butyl lithium, alkali metal alkoxide, potassium-butoxide/molecular sieves, dimethylaminopyridine, $Ti(OCH_2CH_3)_4$ and p-toluenesulfonic acid.

5. Process according to claim 1 wherein said first catalyst is alkali metal alkoxide.

6. Process according to claim 5 wherein said alkali metal alkoxide is selected from the group consisting of sodium methoxide, potassium methoxide, sodium ethoxide and potassium ethoxide.

7. Process according to claim 1 wherein said dipropargyl carbonate is reacted with said alkyl($C_1$–$C_6$)amine to produce said N-alkyl($C_1$–$C_6$) propargyl carbamate in the presence of a second catalyst.

8. Process according to claim 7 wherein said second catalyst is acetic acid.

9. Process according to claim 1 wherein said dialkyl carbonate is dimethyl carbonate, said alkyl($C_1$–$C_6$)amine is butylamine, said first catalyst is sodium methoxide, said second catalyst is acetic acid, and said iodinating agent is a mixture of iodine and sodium hydroxide.

10. Process according to claim 1 wherein said iodinating agent is a mixture of iodine and a base.

* * * * *